(12) United States Patent
Forsyth et al.

(10) Patent No.: US 10,799,283 B2
(45) Date of Patent: Oct. 13, 2020

(54) MULTIPLE LEAD ELECTRODE PROBE FOR CONTROLLED TISSUE ABLATION

(71) Applicant: BOSTON SCIENTIFIC SCIMED, INC., Maple Grove, MN (US)

(72) Inventors: Bruce R. Forsyth, Hanover, MN (US); James P. Rohl, Prescott, WI (US); David J. Lehse, Oakdale, MN (US); Joel T. Eggert, Plymouth, MN (US); Devon N. Arnholt, Shoreview, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 566 days.

(21) Appl. No.: 14/808,483

(22) Filed: Jul. 24, 2015

(65) Prior Publication Data
US 2016/0022353 A1    Jan. 28, 2016

Related U.S. Application Data

(60) Provisional application No. 62/029,818, filed on Jul. 28, 2014.

(51) Int. Cl.
*A61B 18/14* (2006.01)
*A61B 34/10* (2016.01)
(Continued)

(52) U.S. Cl.
CPC .......... *A61B 18/14* (2013.01); *A61B 18/1477* (2013.01); *A61B 18/1492* (2013.01); *A61B 34/10* (2016.02); *A61B 2017/00867* (2013.01); *A61B 2018/00083* (2013.01); *A61B 2018/00136* (2013.01); *A61B 2018/00214* (2013.01); *A61B 2018/00482* (2013.01); (Continued)

(58) Field of Classification Search
CPC . A61B 18/14; A61B 18/1477; A61B 18/1492; A61B 2017/00867; A61B 2018/00083; A61B 2018/00136; A61B 2018/00214; A61B 2018/00482; A61B 2018/00541; A61B 2018/00577; A61B 2018/00875; A61B 2018/009
See application file for complete search history.

(56) References Cited

U.S. PATENT DOCUMENTS 4,311,143 A   1/1982 Komiya
5,370,675 A   12/1994 Edwards et al.
(Continued)

FOREIGN PATENT DOCUMENTS

WO      2014036439 A2    3/2014

*Primary Examiner* — Lee S Cohen
*Assistant Examiner* — Tigist S Demie
(74) *Attorney, Agent, or Firm* — Seager, Tufte & Wickhem, LLC

(57) ABSTRACT

Tissue regions are treated using a multiple lead electrode probe. A plurality of electrodes may be disposed about an elongate shaft. The elongate shaft may be slidably disposed within a lumen of a delivery sheath. One or more probes including one or more electrically active regions may also be slidably disposed within the delivery sheath. The one or more probes may be configured to extend radially about the elongate shaft. The plurality of electrodes and the electrically active regions may be individually connected to a control and power unit through individual channels.

15 Claims, 7 Drawing Sheets

(51) Int. Cl.
   *A61B 18/00*      (2006.01)
   *A61B 17/00*      (2006.01)

(52) U.S. Cl.
   CPC ............... *A61B 2018/00541* (2013.01); *A61B 2018/00577* (2013.01); *A61B 2018/00875* (2013.01); *A61B 2018/00904* (2013.01); *A61B 2018/00982* (2013.01); *A61B 2018/1415* (2013.01); *A61B 2018/1422* (2013.01); *A61B 2018/1435* (2013.01); *A61B 2018/1467* (2013.01); *A61B 2018/1475* (2013.01); *A61B 2034/101* (2016.02); *A61B 2034/104* (2016.02)

(56) References Cited

U.S. PATENT DOCUMENTS

| | | | |
|---|---|---|---|
| 5,507,743 A | 4/1996 | Edwards et al. | |
| 5,827,276 A | 10/1998 | LeVeen et al. | |
| 5,964,754 A | 10/1999 | Osypka | |
| 6,053,937 A | 4/2000 | Edwards et al. | |
| 6,071,279 A * | 6/2000 | Whayne | A61B 18/1492 606/41 |
| 6,108,582 A | 8/2000 | Fischer, Sr. | |
| 6,235,023 B1 | 5/2001 | Lee et al. | |
| 6,402,746 B1 | 6/2002 | Whayne et al. | |
| 6,575,967 B1 | 6/2003 | Leveen et al. | |
| 6,641,580 B1 | 11/2003 | Edwards et al. | |
| 6,652,516 B1 | 11/2003 | Gough | |
| 6,911,019 B2 | 6/2005 | Mulier et al. | |
| 7,025,765 B2 | 4/2006 | Balbierz et al. | |
| 7,195,629 B2 | 3/2007 | Behl et al. | |
| 7,306,595 B2 | 12/2007 | Ostrovsky et al. | |
| 7,329,269 B2 | 2/2008 | Shapiro et al. | |
| 7,416,549 B2 | 8/2008 | Young et al. | |
| 7,419,487 B2 | 9/2008 | Johnson et al. | |
| 7,806,893 B2 | 10/2010 | Ostrovsky et al. | |
| 7,993,334 B2 | 8/2011 | Thistle | |
| 8,211,104 B2 | 7/2012 | McCullagh et al. | |
| 8,398,629 B2 | 3/2013 | Thistle | |
| 2002/0022864 A1 | 2/2002 | Mahvi et al. | |
| 2002/0026127 A1 | 2/2002 | Balbierz et al. | |
| 2002/0026188 A1 * | 2/2002 | Balbierz | A61B 18/1206 606/41 |
| 2002/0133148 A1 | 9/2002 | Daniel et al. | |
| 2002/0156472 A1 | 10/2002 | Lee et al. | |
| 2004/0082948 A1 | 4/2004 | Stewart et al. | |
| 2004/0158239 A1 | 8/2004 | Behl et al. | |
| 2004/0254572 A1 | 12/2004 | McIntyre et al. | |
| 2005/0080409 A1 | 4/2005 | Young et al. | |
| 2005/0101950 A1 | 5/2005 | Gough et al. | |
| 2005/0234444 A1 | 10/2005 | Hooven | |
| 2005/0251239 A1 | 11/2005 | Wallace et al. | |
| 2006/0149226 A1 * | 7/2006 | McCullagh | A61B 18/148 606/41 |
| 2007/0021745 A1 * | 1/2007 | McIntyre | A61B 18/1477 606/41 |
| 2008/0071265 A1 | 3/2008 | Azure | |
| 2011/0022042 A1 | 1/2011 | Randall | |
| 2012/0053576 A1 | 3/2012 | Thistle | |
| 2012/0245665 A1 | 9/2012 | Friedman et al. | |

\* cited by examiner

MULTIPLE LEAD ELECTRODE PROBE FOR CONTROLLED TISSUE ABLATION

CROSS-REFERENCE TO RELATED APPLICATIONS

This application claims priority under 35 U.S.C. § 119 to U.S. Provisional Application Ser. No. 62/029,818, filed Jul. 28, 2014, the entirety of which is incorporated herein by reference.

TECHNICAL FIELD

The present disclosure pertains to medical devices, and methods for manufacturing medical devices. More particularly, the present disclosure pertains to elongated medical devices for ablation of body tissue.

BACKGROUND

The delivery of radiofrequency energy to treatment regions within solid tissue is known for a variety of purposes. Radiofrequency energy may be delivered to diseased regions in target tissue for the purpose of causing tissue necrosis. Electrosurgical probes have been designed for the treatment and necrosis of tumors in the liver and other solid tissues. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

The disclosure is directed to several alternative designs, materials and methods of manufacturing medical device structures and assemblies.

In a first example, a tissue ablation system may comprise a delivery sheath having a proximal end, a distal end, and a lumen extending therebetween, an elongate shaft having a proximal portion and a distal portion, the elongate shaft slidably disposed within the lumen of the delivery sheath, a first helically wound electrode disposed about the distal portion of the elongate shaft, the first helically wound electrode having a first length, a second helically wound electrode disposed about the distal portion of the elongate shaft, the second helically wound electrode having a second length less than the first length, a third helically wound electrode disposed about the distal portion of the elongate shaft, the third helically wound electrode having a third length less than the second length, a plurality probes slidably disposed within the delivery sheath, the plurality of probes configured to move between a compressed configuration and an expanded configuration, at least one electrically conductive region on each of the probes of the plurality of probes, and a power and control unit in electrically communication with the first helically wound electrode, the second helically wound electrode, the third helically wound electrode, and the at least one electrically conductive region on the each of the probes of the plurality of probes.

Alternatively or additionally to any of the examples above, in another example, the first helically wound electrode, the second helically wound electrode, the third helically wound electrode, and the at least one electrically conductive region on the each of the probes of the plurality of probes are electrically connected to the power and control unit through individual c Alternatively or additionally to any of the examples above, in another example, each of the probes of the plurality of probes is individually slidable within the delivery sheath.

Alternatively or additionally to any of the examples above, in another example, the plurality of probes are configured to transform from a collapsed configuration to a radially expanded configuration when the one or more probes are distally advanced beyond the distal end of the delivery sheath.

Alternatively or additionally to any of the examples above, in another example, the plurality of probes comprise shape memory alloy Alternatively or additionally to any of the examples above, in another example, an insulating coating is disposed over the shape memory alloy.

Alternatively or additionally to any of the examples above, in another example, the at least one electrically conductive region on each of the probes of the plurality of probes are regions of the probe free of the insulating coating.

Alternatively or additionally to any of the examples above, in another example, the distal end of the elongate shaft comprises a piercing element.

Alternatively or additionally to any of the examples above, in another example, a distal end region of each of the plurality of probes comprises a spear-like shape.

Alternatively or additionally to any of the examples above, in another example, the plurality of probes comprises at least three probes.

Alternatively or additionally to any of the examples above, in another example, a method of ablating tissue may comprise advancing a tissue ablation system to a target region, the tissue ablation system may comprise a delivery sheath having a proximal end, a distal end, and a lumen extending therebetween, an elongate shaft having a proximal end and a distal end slidably disposed within the lumen of the delivery sheath, a first helically wound electrode disposed about the elongate shaft, a second helically wound electrode disposed about the elongate shaft, a first probe slidably disposed within the delivery sheath, the first probe including a first electrically conductive region disposed adjacent a distal end thereof, and a second probe slidably disposed within the delivery sheath, the second probe including a second electrically conductive region disposed adjacent a distal end thereof, positioning the distal end of the elongate shaft adjacent to a first end of the target region, advancing the first probe distally beyond a distal end of the delivery sheath, delivering energy between the first helically wound electrode the first electrically conductive region, repositioning at least one of the first or second probes, and subsequently delivering energy between the repositioned at least one of first or second probes and at least one of the first helically wound electrode or the second helically wound electrode.

Alternatively or additionally to any of the examples above, in another example, advancing the first probe distally beyond a distal end of the delivery sheath comprises positioning the first electrically conductive region adjacent an outer edge of the target tissue.

Alternatively or additionally to any of the examples above, in another example, prior to delivering energy to the first helically wound electrode and the first conductive region, the target tissue is mapped using impedance measurements.

Alternatively or additionally to any of the examples above, in another example, prior to delivering energy to the first helically wound electrode and the first conductive region, an ablation is simulated electronically using the impedance measurements.

Alternatively or additionally to any of the examples above, in another example, repositioning at least one of the first or second probes a second time and subsequently delivering energy between the repositioned at least one of first or second probes and at least one of the first helically wound electrode or the second helically wound electrode.

Alternatively or additionally to any of the examples above, in another example, a tissue ablation system may comprise a delivery sheath having a proximal end, a distal end, and a lumen extending therebetween, an elongate shaft having a proximal end and a distal end slidably disposed within the lumen of the delivery sheath, at least one helically wound electrode disposed about the elongate shaft, one or more probes slidably disposed within the delivery sheath, and at least one electrically conductive region on the one or more probes.

Alternatively or additionally to any of the examples above, in another example, the one or more probes are configured to transform from a collapsed configuration to a radially expanded configuration when the one or more probes are distally advanced beyond the distal end of the delivery sheath.

Alternatively or additionally to any of the examples above, in another example, the one or more probes comprises a shape memory alloy.

Alternatively or additionally to any of the examples above, in another example, the one or more probes comprise an insulating coating disposed over the shape memory alloy.

Alternatively or additionally to any of the examples above, in another example, the at least one electrically conductive region on the one or more probes are regions of the probe free of the insulating coating.

Alternatively or additionally to any of the examples above, in another example, the one or more probes are individually actuatable.

Alternatively or additionally to any of the examples above, in another example, the at least one helically wound electrode and the at least one electrically conductive region on the one or more probes are electrically connected to a power and control unit through individual channels.

Alternatively or additionally to any of the examples above, in another example, a distal end region of the one or more probes comprises a spear-like shape.

Alternatively or additionally to any of the examples above, in another example, the one or more probes comprises a helically wound filament.

Alternatively or additionally to any of the examples above, in another example, a tissue ablation system may comprise a delivery sheath having a proximal end, a distal end, and a lumen extending therebetween, an elongate shaft having a proximal portion and a distal portion, the elongate shaft slidably disposed within the lumen of the delivery sheath, a first helically wound electrode disposed about the distal portion of the elongate shaft, the first helically wound electrode having a first length, a second helically wound electrode disposed about the distal portion of the elongate shaft, the second helically wound electrode having a second length less than the first length, a third helically wound electrode disposed about the distal portion of the elongate shaft, the third helically wound electrode having a third length less than the second length, a plurality probes slidably disposed within the delivery sheath, the plurality of probes configured to move between a compressed configuration and an expanded configuration, at least one electrically conductive region on each of the probes of the plurality of probes, a power and control unit in electrically communication with the first helically wound electrode, the second helically wound electrode, the third helically wound electrode, and the at least one electrically conductive region on the each of the probes of the plurality of probes.

Alternatively or additionally to any of the examples above, in another example, the at least the first helically wound electrode, the second helically wound electrode, the third helically wound electrode, and the at least one electrically conductive region on the each of the probes of the plurality of probes are electrically connected to the power and control unit through individual channels.

Alternatively or additionally to any of the examples above, in another example, each of the probes of the plurality of probes is individually slidable within the delivery sheath.

Alternatively or additionally to any of the examples above, in another example, the plurality of probes are configured to transform from a collapsed configuration to a radially expanded configuration when the one or more probes are distally advanced beyond the distal end of the delivery sheath.

Alternatively or additionally to any of the examples above, in another example, the plurality of probes comprise shape memory alloy and an insulating coating disposed over the shape memory alloy.

Alternatively or additionally to any of the examples above, in another example, the distal end of the elongate shaft comprises a piercing element.

Alternatively or additionally to any of the examples above, in another example, a method of ablating tissue may comprise advancing a tissue ablation system to a target region, the tissue ablation system may comprise a delivery sheath having a proximal end, a distal end, and a lumen extending therebetween, an elongate shaft having a proximal end and a distal end slidably disposed within the lumen of the delivery sheath, a first helically wound electrode disposed about the elongate shaft, a second helically wound electrode disposed about the elongate shaft, a first probe slidably disposed within the delivery sheath, the first probe including a first electrically conductive region disposed adjacent a distal end thereof, and a second probe slidably disposed within the delivery sheath, the second probe including a second electrically conductive region disposed adjacent a distal end thereof, positioning the distal end of the elongate shaft adjacent to a first end of the target region, advancing the first probe distally beyond a distal end of the delivery sheath, delivering energy between the first helically wound electrode the first electrically conductive region, repositioning at least one of the first or second probes, and subsequently delivering energy between the repositioned at least one of first or second probes and at least one of the first helically wound electrode or the second helically wound electrode.

Alternatively or additionally to any of the examples above, in another example, advancing the first probe distally beyond a distal end of the delivery sheath comprises positioning the first electrically conductive region adjacent an outer edge of the target tissue.

Alternatively or additionally to any of the examples above, in another example, prior to delivering energy to the first helically wound electrode and the first conductive region, the target tissue is mapped using impedance measurements.

Alternatively or additionally to any of the examples above, in another example, prior to delivering energy to the first helically wound electrode and the first conductive region, an ablation is simulated electronically using the impedance measurements.

Alternatively or additionally to any of the examples above, in another example, repositioning at least one of the first or second probes a second time and subsequently delivering energy between the repositioned at least one of first or second probes and at least one of the first helically wound electrode or the second helically wound electrode.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments in connection with the accompanying drawings, in which.

Figure 1:
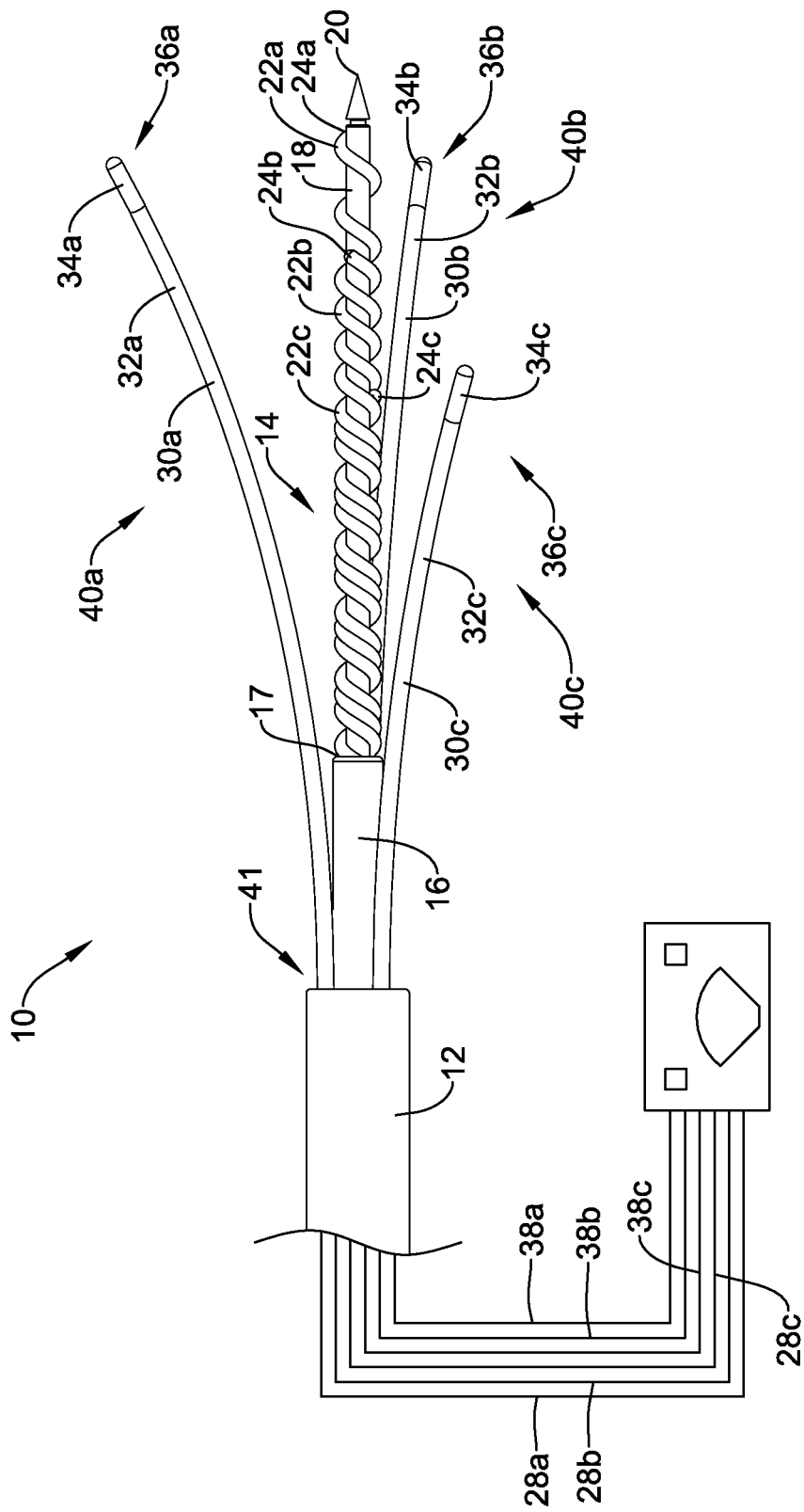
FIG. 1 is side view of a distal end of an illustrative multiple lead ablation system.

While the disclosure is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

In some treatments, an ablation tool using radiofrequency (RF) energy can be inserted in or near a desired treatment region to thermally destroy or ablate the surrounding tissue in a controlled manner. In a specific application of lung cancer or pulmonary disease treatment, an ablation tool using RF energy can be inserted in or near a suspected carcinoma tumor to thermally destroy the surrounding tissue in a controlled ramp and duration of treatment. In some instances, a multiple electrode assembly may allow for independent control of the separate probe assemblies to provide better and more uniform distribution of the surrounding tissue temperature and provide a homogeneous heating and ablation zone for tissue necrosis. It is contemplated that a multiple electrode assembly may also be used in the treatment of cancerous masses, lesions or tumors within other parts of the body, such as, but not limited to the stomach, pancreas, liver, breast, brain, esophagus, etc. It is further completed that devices and methods described herein may be used within an arterial application.

FIG. 1 is a side view of a distal end of an illustrative multiple lead ablation system 10 for use in ablating tissue. The system 10 may include an elongate shaft 14 slidably disposed within a central lumen 41 of the delivery sheath or guide catheter 12. The delivery sheath 12 may extend proximally from a distal end to a proximal end configured to remain outside the body. The lumen 41 may extend from the proximal end to distal end of the delivery sheath 12. In some instances, the delivery sheath 12 may be advanced through a bronchoscope, endoscope, or gastroscope. In some instances, the elongate shaft 14 may have a proximal portion 16 and a distal portion 18. In some embodiments, the proximal portion 16 may have a larger cross-section than the distal portion 18, although this is not required. It is contemplated that in some embodiments, the elongate shaft 14 may have a uniform cross-section along the entire length thereof. The elongate shaft 14 may transition from a proximal portion 16 have a first cross-sectional area to a distal portion 18 have a second cross-sectional area in a step-wise manner or gradually transition. In some embodiments, the cross-sectional area for the proximal portion 16 may be larger than the cross-sectional area of the distal portion 18, although the reverse configuration is contemplated. The elongate shaft 14 may extend proximally from a distal end 20 to a proximal end (not shown) configured to remain outside the body. The proximal end may include a hub (not explicitly shown) attached thereto for connecting other treatment devices or providing a port for facilitating other treatments. It is contemplated that the stiffness of the elongate shaft 14 may be modified to form an ablation system 10 for use in various locations within the body. To this end, the material used for manufacturing the elongate shaft 14 may include any suitable biocompatible material such as, but are not limited to, polymers, metals, alloys, either in combination or alone. The distal end 20 of the elongate shaft 14 include a piercing element or may be sharpened or pointed to facilitate the advancement of the elongate shaft 14 through tissue, although this is not required.

The ablation system 10 may further include a plurality of helically wound electrodes 22a, 22b, 22c (collectively 22) disposed about the distal portion 18 of the elongate shaft 14. While the electrodes 22 are described as radiofrequency electrodes, it is contemplated that other methods and devices for raising the temperature of the tissue may be used, such as, but not limited to: ultrasound, microwave, or other acoustic, optical, electrical current, direct contact heating, or other heating. While the system 10 is illustrated as including three helically wound electrodes 22, it is contemplated that the ablation system 10 may include any number of helically wound electrodes 22 desired, such as, but not limited to, one, two, three, or more. It is further completed that while the electrodes 22 are described as helically wound, other configurations are contemplated. For example, the electrodes 22 may extend generally parallel to a longitudinal axis of the elongate shaft 14. In other instances, the electrodes 22 may be discrete elements secured or otherwise formed on an outer surface of the elongate shaft 14. The electrodes 22 may be longitudinally and/or radially and/or circumferentially spaced as desired. The pitch (or distance between adjacent windings) of the electrodes 22 may be varied as desired.

It is contemplated that the electrodes 22 may extend over varying lengths of the distal portion 18 of the elongate shaft 14 to allow for customization of the treatment region. For example, the first helically wound electrode 22a may extend distally from a junction 17 between the proximal portion 16 and the distal portion 18 to a point proximal to the distal end 20 of the elongate shaft 14. The second helically wound electrode 22b may extend distally from the junction 17 between the proximal portion 16 and the distal portion 18 to a point proximal to a distal end 24a of the first helically wound electrode 22a. The third helically wound electrode 22c may extend distally from the junction 17 between the proximal portion 16 and the distal portion 18 to a distal end 24c proximal to a distal end 24b of the second helically wound electrode 22b. In some instances, the electrodes 22 may extend proximally beyond the junction 17, although this is not required. The electrodes 22 may be formed from any suitable material such as, but not limited to, platinum, gold, stainless steel, cobalt alloys, or other non-oxidizing materials. In some instances, titanium, tantalum, or tungsten may be used. Portions of the electrodes 22 may be coated with an insulating or semi-insulating coating with regions of the coating removed to create conductive regions. In some instances, the electrodes 22 may be coated with parylene or other insulating material. In other instances, the coating may be formed of semi-insulating materials, such as but not limited to a porous polymer or a ceramic. It is further contemplated that the coating may be a very thin polymer or coating. The coating may electrically isolate the electrodes 22a, 22b, 22c from one another and allow for independent control of the each of the electrodes 22a, 22b, 22c.

In some embodiments, the electrodes 22a, 22b, 22c may be electrically connected individually to a power and control element 26 through separate electrical conductors 28a, 28b, 28c (collectively 28). In some instances, the electrical conductors 28 may be an extension of the helically wound electrodes 22. In other instances, the electrical conductors 28 may be separate members in electrical communication with the electrodes 22. In some embodiments, the electrical conductors 28 may be disposed within a lumen of the elongate shaft 14 while in other embodiments, the electrical conductors 28 may be embedded in a wall of the elongate shaft 14.

The ablation system 10 may further include a plurality of radially extending arms or probes 30a, 30b, 30c (collectively 30). While the system 10 is illustrated as including three radially extending probes 30, it is contemplated that the ablation system 10 may include any number of radially extending probes 30 desired, such as, but not limited to, one, two, three, or more. The probes 30 may extend proximally from a distal end region 36a, 36b, 36c (collectively 36) to a proximal end (not shown) configured to remain outside the body. The proximal ends may be individually manipulated to provide for independent longitudinal movement of the probes 30. In some embodiments, the distal end regions 36 of the probes 30 may be sharpened or pointed to facilitate the advancement of the probes 30 through tissue, although this is not required.

In some instances, the probes 30 may be formed from shape memory alloys, enabling the probes 30 to assume a curved profile when advanced distally from the delivery sheath 12, as will be discussed in more detail below. For example, the probes 30 can be formed from alloys such as, but not limited to, nitinol or Elgiloy®. In some embodiments, the probes 30 may be formed from a conductive material covered with an insulating or semi-insulating coating 32a, 32b, 32c (collectively 32). The probes 30 may be coated with insulating material using any number of coating techniques, such as, but not limited to, dip coating, spray coating, etc. In some instances, the probes 30 may be coated with parylene or other insulating material. In some instances, the coating 32 may be formed of semi-insulating materials, such as but not limited to a porous polymer or a ceramic. It is further contemplated that the coating 32 may be a very thin polymer or coating.

It is contemplated that the coating 32 may be removed from or not applied to one or more locations on the probes 30 to form one or more electrode pads or electrically conductive regions 34a, 34b, 34c (collectively 34) configured to deliver RF energy to a target region. In some embodiments, the electrically conductive regions 34a, 34b, 34c may be formed at or adjacent to a distal end region 36a, 36b, 36c of the probes 30. While the probes 30 are illustrated as including a single electrically conductive region 34 on each probe 30, it is contemplated that more than one electrically conductive region 34 may be formed on each probe 30, as desired. It is further contemplated that the probes 30 need not include the same number of electrically conductive regions 34 on each probe.

The probes 30 may be slidably disposed within a lumen 41 of the delivery sheath 12 such that the probes 30a, 30b, 30c can be advanced distally and proximally retracted individually. In some embodiments, the delivery sheath 12 may include features to maintain a desired circumferential spacing of the probes 30. For example, the wall of the delivery sheath 12 may be formed with three separate lumens therein for advancing each of the probes 30a, 30b, 30c through. In other instances, an inner wall of the delivery sheath 12 may include protrusions or other aligning features to maintain a desired spacing of the probes 30.

The probes 30 may be formed from a shape memory material and having a curved distal portion 40a, 40b, 40c (collectively 40). The probes 30 may be temporarily deformed to assume a generally straight configuration for advancement within the delivery sheath 12 to the desired treatment location. The delivery sheath 12 may be formed of a suitable material to maintain the probes 30 in a biased, or collapsed, configuration. As a probe 30 is advanced distally out of the delivery sheath 12 (or as the delivery sheath 12 is proximally retracted) the distal portion 40 may regain its curved configuration. The distal end region 36 may expand radially outward from the elongate shaft 14 as it is distally advanced out of the delivery sheath 12. It is contemplated that the radial distance between the distal end region 36 and the elongate shaft 14 may be controlled in part by the length of the probe 30 extending from the delivery sheath 12 and the radius of curvature of the distal portion 40. It is contemplated that each of the probes 30a, 30b, 30c may have distal portions 40a, 40b, 40c with different degrees of curvatures such that each probe 30, when fully deployed, extends a different radial distance from the elongate shaft 14. As used herein, the term "fully deployed" indicates that the curved or shaped portion of the probe 30 is fully extended from the delivery sheath. This may allow a physician to customize the treatment region to more efficiently ablate non-spherical or non-uniform target regions. For example, when fully deployed, the first probe 30a may extend a first radial distance from the elongate shaft 14, the second probe 30b may extend a second radial distance from the elongate shaft 14, and the third probe 30c may extend a third radial distance from the elongate shaft 14. In some embodiments, the first radial distance may be greater than the second radial distance and the second radial distance may be greater than the third radial distance. This is just an example. It is contemplated that the distal portions 40 of the probes 30 may be formed in any shape and having any radial distance in the fully deployed configuration desired. In some instances, the probes 30 may be formed with distal portions 40 having similar or the same degrees of curvature.

In some embodiments, the electrically conductive regions 34a, 34b, 34c may be electrically connected individually to a power and control element 26 through separate electrical conductors 38a, 38b, 38c (collectively 38). In some instances, the electrical conductors 38 may be an extension of the probes 30. In other instances, the electrical conductors 38 may be separate members in electrical communication with the probes 30 and the electrically conductive regions 34.

The control and power unit 26 may include monitoring elements to monitor parameters such as power, voltage, pulse size, temperature, force, contact, pressure, impedance and/or shape and other suitable parameters, with sensors mounted along the ablation system 10, as well as suitable controls for performing the desired procedure. In some embodiments, the power unit may control the radiofrequency (RF) electrodes 22 and electrically conductive regions 34. The electrodes 22 and electrically conductive regions 34 may be configured to operate at a suitable frequency and generate a suitable signal. It is further contemplated that other ablation devices may be used as desired, for example, but not limited to resistance heating, ultrasound, microwave, and laser devices and these devices may require that power be supplied by the power unit 26 in a different form.

Each electrode 22a, 22b, 22c and each electrically conductive region 34a, 34b, 34c may be connected to individual channels of the control and power unit 26 through separate electrical conductors 28a, 28b, 28c, 38a, 38b, 38c. As each electrode 22a, 22b, 22c and each electrically conductive region 34a, 34b, 34c may be individually connected to a separate grounding in channels of the control and power unit 26; power may be individually supplied and adjusted. For example, it is contemplated that each channel may include a separate variable resistor for individually adjusting each individual circuit. It is contemplated that the control and power unit 26 may include any number of channels desired such that the electrical connections between the control and power unit 26 and the electrodes 22a, 22b, 22c and the electrically conductive regions 34a, 34b, 34c may be individually adjusted. It is further contemplated that a separate processor or processing unit may be supplied in addition to the control and power unit 26.

Referring now to FIGS. 2-5, there is illustrated an illustrative method in which ablation system 10 may be used to thermally ablate tumor tissue 42. While not explicitly shown, it is contemplated that prior to, or during treatment, the treatment region may be visualized, for example, using ultrasound or computerized tomography (CT) technologies. In some instances, the target tissue may be measured using visual markers. Due to the typically irregular shape of cancerous masses, tumors, and/or lesions, it may be desirable to know the size and shape of the treatment region prior to beginning ablation. For example, if one were to underestimate the size of the treatment region, it may be difficult to ablate tissue beyond what may have already been ablated.

Figure 2:
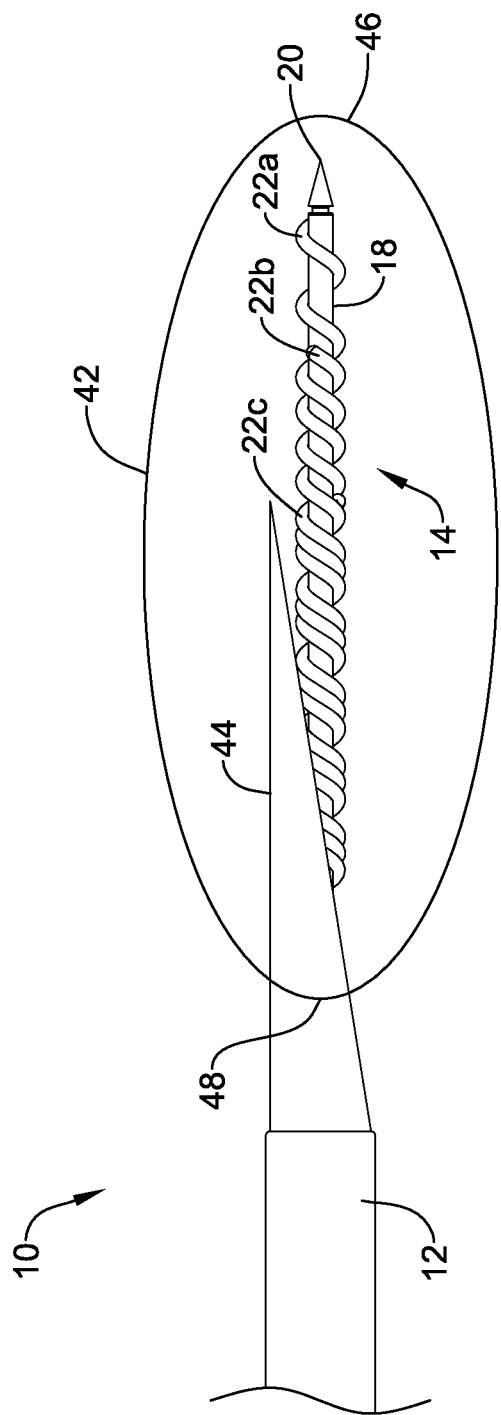
FIGS. 2-5 illustrate an illustrative method in which an ablation system may be used to thermally ablate tissue.

Referring to FIG. 2, once the tumor tissue 42 has been located, the ablation system 10 may be placed using known techniques. In some embodiments, a piercing element or needle 44 may be used to facilitate delivery of the ablation system to the treatment region. For example, the needle 44 may be used to pass the system 10 through cartilage or other fibrous anatomy, such as, but not limited to the lining of the stomach or the bronchial walls. The needle 44 may be slidably disposed within the delivery sheath 12 and may be retracted into the delivery sheath or from the body during the ablation procedure. It is further contemplated that the ablation system 10 may be rotated to facilitate penetration into the treatment region. In some instances, the ablation system 10 may be used in tandem with a helical coring needle (not explicitly shown) to gain access to peripheral nodules. A helical coring needle may also be used to obtain a biopsy sample from the treatment region. A rapid test on the biopsy sample may be used to confirm the tumor tissue 42 should be ablated.

The elongate shaft 14 may be advanced distally out of the delivery sheath 12 until the distal end 20 is adjacent to a first end 46 of the tumor tissue 42. In some embodiments, the elongate shaft 14 may be rotated as it is advanced through the tumor tissue 42. In some instances, this may increase the surface area of the electrodes 22 in contact with the tissue 42. It is contemplated that the ablation system 10 may be operated in a bipolar mode, or multi-polar mode, or without the use of external ground pads. In a bipolar mode, the electrodes 22 and the electrically conductive regions 34 may be 180° out of phase such that one of the electrodes 22 or one of the electrically conductive regions 34 acts as the ground electrode (e.g. one cathode and one anode). Once the elongate shaft 14 has been positioned, one or more of the probes 30 may be advanced from the delivery sheath 12. While not explicitly shown, impedance may be used to determine the location and/or size and/or shape of the tumor tissue 42. As discussed above, each of the electrodes 22a, 22b, 22c and each of the electrically conductive regions 34a, 34b, 34c may be connected to the control and power unit through separate channels. As such, power may delivered through various combinations of the electrodes 22a, 22b, 22c and the electrically conductive regions 34a, 34b, 34c to map the tumor tissue 42 and determine is the ablation system 10 is appropriately located. For example, a circuit may be formed between the electrically conductive region 34a on the first probe 30a and the first helically wound electrode 22a. Different combinations of probes 30 and helically wound electrodes 22 can be used to allow for three dimensional vector control of impedance measurements and ablation.

Figure 3:
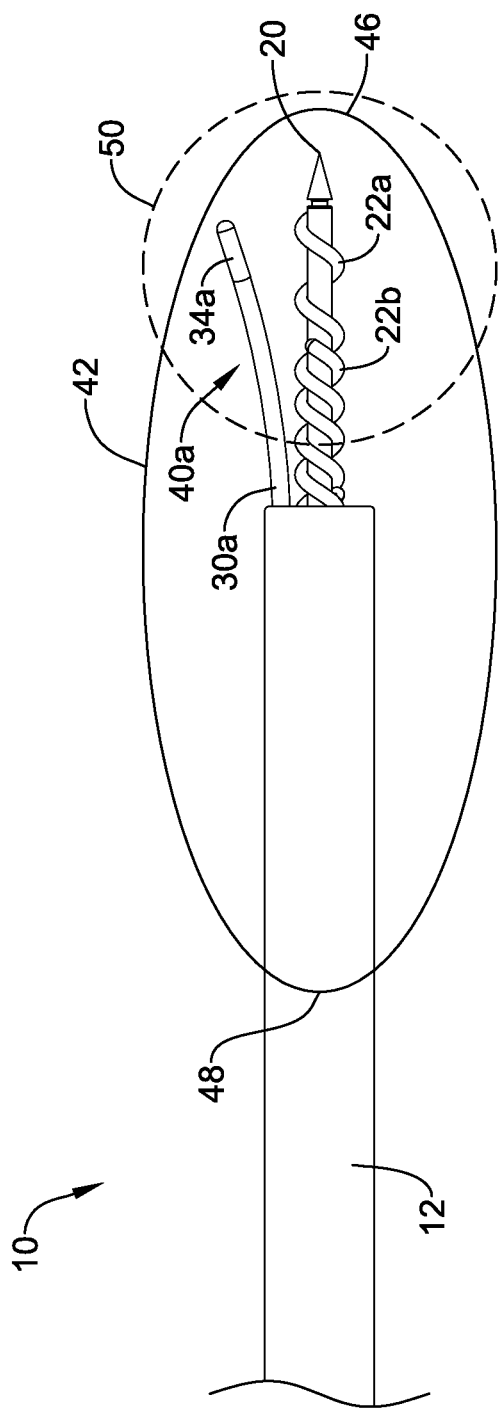

Once the location of the ablation system 10 has been confirmed, the ablation system 10 may be positioned in a first treatment configuration, as shown in FIG. 3. For example, the elongate shaft 14 may be advanced distally out of the delivery sheath 12 until the distal end 20 is adjacent to a first end 46 of the tumor tissue 42. The delivery sheath 12 may be distally advanced, or proximally retracted as necessary to expose a desired length of one or more of the helically wound electrodes 34. For example, in some instances, it may be desirable to pass electrical current between the first electrically active region 34a and only a distal portion 52a of the first helically wound electrode 22a. In such an instance, the delivery sheath 12 may be advanced to cover (and electrically insulate) a proximal portion of the first helically wound electrode 22a. A portion of the second helically wound electrode 22b and/or the third helically wound electrode 22c may be exposed. However, as the helically wound electrodes 22 are connected to the control unit 26 through separate channels, current may pass between an active electrode 22 and an active probe 30 as selected by the user. In some instances, it may be desirable to begin the ablation procedure at a first end 46 of the tumor tissue and move towards a second end 48 of the tumor tissue. In such an instance, it may be desirable for the distal-most electrode 22a to be selected as the active electrode in the initial ablation.

One of the probes 30a may be advanced from the delivery sheath 12 until it is located at the desired radial distance from the elongate shaft 14. For example, the electrically conductive region 34a may be positioned near an outer perimeter or edge of the tumor tissue 42. Once the probe 30a has been advanced to the desired region, energy may be supplied between the first electrode 22a and the first electrically active region 34a. The remaining electrodes 22b, 22c and/or electrically active regions 34b, 34c may be "off" or electrically insulated. The amount of energy delivered to the ablation electrode may be determined by the desired treatment as well as the feedback obtained from the system 10. The power level and duration of the ablation may be adjusted accordingly based on the impedance of the tissue. For example, more energy may result in a larger, deeper lesion. A lesion 50 may be formed that is proportional in size to the length of the exposed helically wound electrode 22a and the radial distance between the electrically active region 34a and the helically wound electrode 22a. The physician may continue to select different vectors (e.g. different combinations of electrically active regions 34 and electrodes 22) to treat and/or ablate the desired region. While not explicitly shown, it may be desirable to advance one or both of the second or third probe 30b, 30c to create lesions at different radial locations in accordance with the geometry of the tumor tissue 42.

Figure 4:
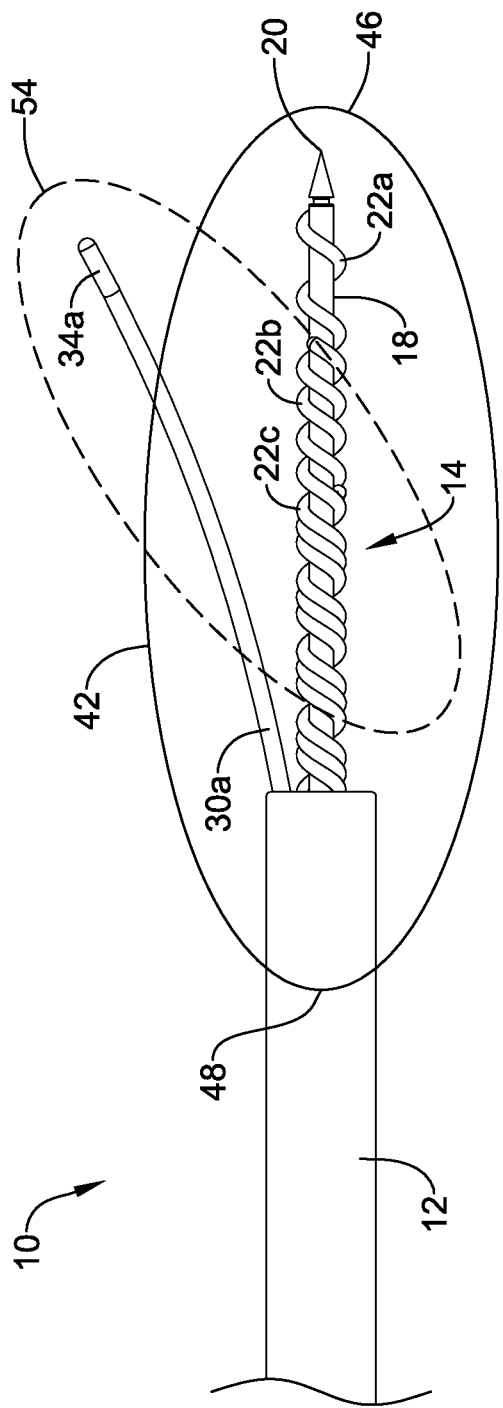

Referring now to FIG. 4, to continue treatment towards the second end 48 of the tumor tissue, the physician may retract the delivery sheath 12 to expose a greater length of helically wound electrode 22. In some instances, the first probe 30a may be manipulated to position the electrically active region 34a at a different radial distance from the elongate shaft 14 relative to the preceding treatment configuration, although this is not required. It is contemplated that the desired radial distance of the electrically active region 34 of the probes 30 is determined by the size and shape of the target treatment region. Once the probe 30a has been advanced to the desired region, energy may be supplied between the second helically wound electrode 22b and the first electrically active region 34a. The remaining electrodes 22a, 22c and/or electrically active regions 34b, 34c may be "off" and/or electrically insulated. The amount of energy delivered to the ablation electrode may be determined by the desired treatment as well as the feedback obtained from the system 10. The power level and duration of the ablation may be adjusted accordingly based on the impedance of the tissue. For example, more energy may result in a larger, deeper lesion. A lesion 54 may be formed that is proportional in size to the length of the exposed helically wound electrode 22a and the radial distance between the electrically active region 34a and the second helically wound electrode 22b.

Figure 5:
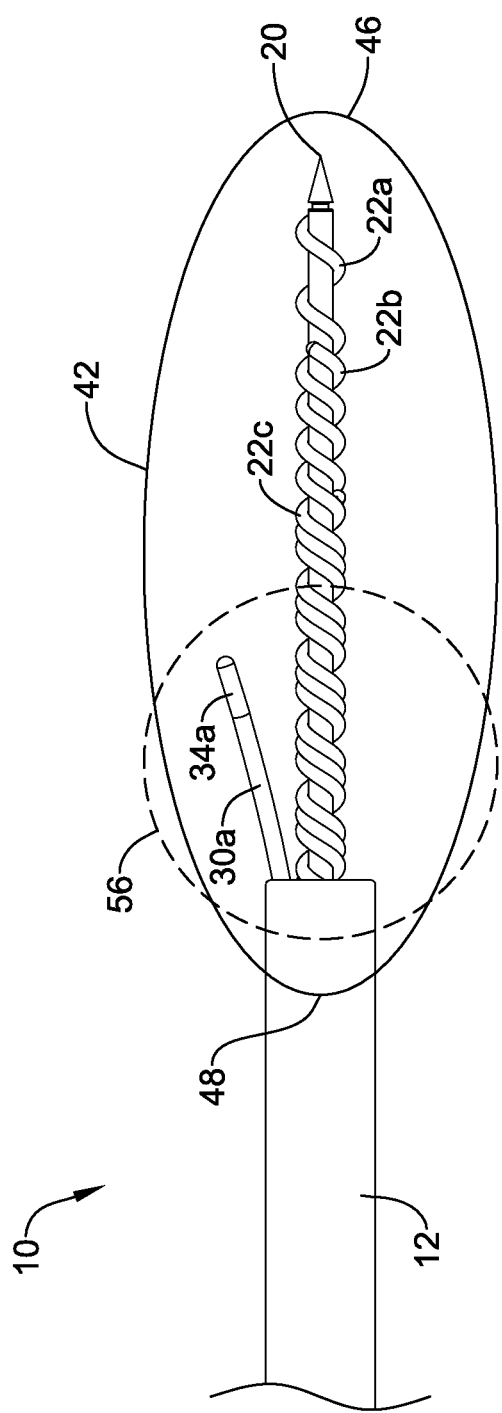

Referring now to FIG. 5, to continue treatment towards the second end 48 of the tumor tissue, the physician may retract the delivery sheath 12, if necessary, to expose a greater length of helically wound electrode 22. In some instances, the first probe 30a may be manipulated to position the electrically active region 34a at a different radial distance from the elongate shaft 14 relative to the preceding treatment configuration, although this is not required. It is contemplated that the desired radial distance of the electrically active region 34 of the probes 30 is determined by the size and shape of the target treatment region. Once the probe 30a has been advanced to the desired region, energy may be supplied between the third helically wound electrode 22c and the first electrically active region 34a. The remaining electrodes 22a, 22b and/or electrically active regions 34b, 34c may be "off" and/or electrically insulated. The amount of energy delivered to the ablation electrode may be determined by the desired treatment as well as the feedback obtained from the system 10. The power level and duration of the ablation may be adjusted accordingly based on the impedance of the tissue. For example, more energy may result in a larger, deeper lesion. A lesion 56 may be formed that is proportional in size to the length of the exposed helically wound electrode 22a and the radial distance between the electrically active region 34a and the third helically wound electrode 22c.

The physician may continue to select different vectors (e.g. different combinations of electrically active regions 34 and electrodes 22) to treat and/or ablate the desired region. Independent control of the electrodes 22 and the electrically active regions 34 may provide better and more uniform temperature distribution through the surrounding tissue and provide a homogenous heating and ablation zone for tissue necrosis. It is further contemplated that increased control over the ablation zone may reduce undesired tissue scarring. The ablation procedure may be a series of short ablations alternated with repositioning of the probes 30 to ablate the desired geometry. While not explicitly shown, it may be desirable to advance one or both of the second or third probe 30b, 30c to create lesions at different radial locations in accordance with the geometry of the tumor tissue 42. It is contemplated that in some instances, the probes 30a, 30b, 30c may be deployed simultaneously or in various combinations thereof to ablate a larger region.

It is contemplated that the ablation system 10 may be used in combination with automated controls. In some instances, the size and/or shape of the treatment region may be determined using imaging procedures prior to the ablation procedure. A map of the treatment region may be utilized to determine an appropriate ablation sequence. For example, computer and/or simulation software may be utilized to determine the desired position of the probes 30 and/or the power level and duration of the ablation at each probe 30 and electrode 22 configuration. In some instances, the software package may be configured to provide positional instructions to a physician controlling the ablation system 10. In other instances, the ablation system 10 may further include a servo motor or other control means and the software package may automatically control the positions of the probes 30 and other ablation parameters such as, but not limited to, power and/or duration. It is contemplated that software may be provided to simulate a treatment prior to performing the treatment. This may facilitate the selection of appropriate probe 30 positions, power level, and duration of treatment. It is further contemplated that impedance sensing may be used to "pre-read" the treatment region to facilitate the selection of the appropriate power level and duration of treatment.

Figure 6:
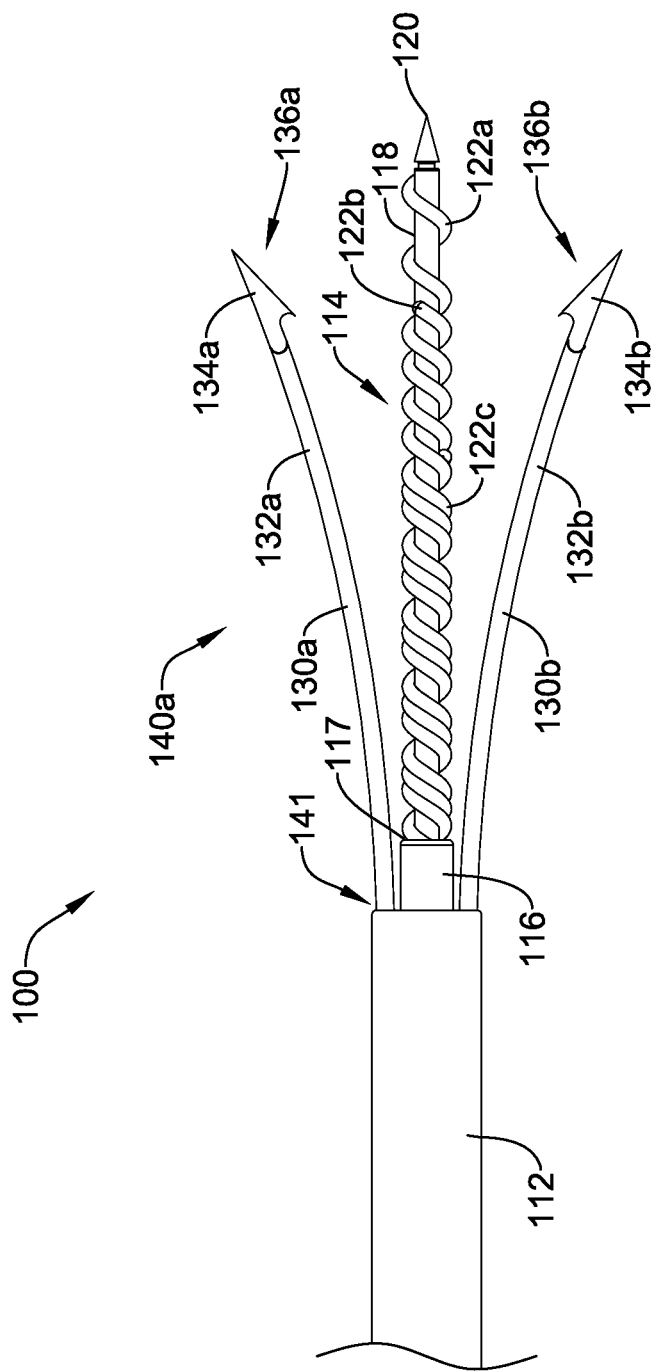
FIG. 6 is side view of a distal end of another illustrative multiple lead ablation system.

FIG. 6 is a side view of a distal end of another illustrative multiple lead ablation system 100 for use in ablating tissue. The system 100 may include an elongate shaft 114 slidably disposed within a lumen 140 of the delivery sheath or guide catheter 112. In some instances, the delivery sheath 112 may be advanced through a bronchoscope, endoscope, or gastroscope. In some instances, the elongate shaft 114 may have a proximal portion 116 and a distal portion 118. In some embodiments, the proximal portion 116 may have a larger cross-section than the distal portion 118, although this is not required. It is contemplated that in some embodiments, the elongate shaft 114 may have a uniform cross-section along the entire length thereof. The elongate shaft 114 may transition from a proximal portion 116 have a first cross-sectional area to a distal portion 118 have a second cross-sectional area in a step-wise manner or gradually transition. In some embodiments, the cross-sectional area for the proximal portion 116 may be larger than the cross-sectional area of the distal portion 118, although the reverse configuration is contemplated. The elongate shaft 114 may extend proximally from a distal end 120 to a proximal end (not shown) configured to remain outside the body. The proximal end may include a hub (not explicitly shown) attached thereto for connecting other treatment devices or providing a port for facilitating other treatments. It is contemplated that the stiffness of the elongate shaft 114 may be modified to form an ablation system 100 for use in various locations within the body. To this end, the material used for manufacturing the elongate shaft 114 may include any suitable biocompatible material such as, but are not limited to, polymers, metals, alloys, either in combination or alone. The distal end 120 of the elongate shaft 114 may be sharpened or pointed to facilitate the advancement of the elongate shaft 114 through tissue, although this is not required.

The ablation system 100 may further include a plurality of helically wound electrodes 122a, 122b, 122c (collectively 122) disposed about the distal portion 118 of the elongate shaft 114. The electrodes 122 may be similar in form and function to the electrodes 22 described above. While the system 100 is illustrated as including three helically wound electrodes 122, it is contemplated that the ablation system 100 may include any number of helically wound electrodes 122 desired, such as, but not limited to, one, two, three, or more. It is further completed that while the electrodes 122 are described as helically wound, other configurations are contemplated. For example, the electrodes 122 may extend generally parallel to a longitudinal axis of the elongate shaft 114. In other instances, the electrodes 122 may be discrete elements secured or otherwise formed on an outer surface of the elongate shaft 114. The electrodes 122 may be longitudinally and/or radially and/or circumferentially spaced as desired. The pitch (or distance between adjacent windings) of the electrodes 122 may be varied as desired.

It is contemplated that the electrodes 122 may extend over varying lengths of the distal portion 118 of the elongate shaft 114 to allow for customization of the treatment region. For example, the first helically wound electrode 122a may extend distally from a junction 117 between the proximal portion 116 and the distal portion 118 to a point proximal to the distal end 120 of the elongate shaft 114. The second helically wound electrode 122b may extend distally from the junction 117 between the proximal portion 116 and the distal portion 118 to a point proximal to a distal end of the first helically wound electrode 122a. The third helically wound electrode 122c may extend distally from the junction 117 between the proximal portion 116 and the distal portion 118 to a distal end proximal to a distal end of the second helically wound electrode 122b. In some instances, the electrodes 122 may extend proximally beyond the junction 117, although this is not required. The electrodes 122 may be formed from any suitable material such as, but not limited to, platinum, gold, stainless steel, cobalt alloys, or other non-oxidizing materials. In some instances, titanium, tantalum, or tungsten may be used. Portions of the electrodes 122 may be coated with an insulating or semi-insulating coating with regions of the coating removed to create conductive regions. In some instances, the electrodes 122 may be coated with parylene or other insulating material. In other instances, the coating may be formed of semi-insulating materials, such as but not limited to a porous polymer or a ceramic. It is further contemplated that the coating may be a very thin polymer or coating. The coating may electrically isolate the electrodes 122a, 122b, 122c from one another and allow for independent control of the each of the electrodes 122a, 122b, 122c.

In some embodiments, the electrodes 122a, 122b, 122c may be electrically connected individually to a power and control element through separate electrical conductors. In some instances, the electrical conductors may be an extension of the helically wound electrodes 122. In other instances, the electrical conductors may be separate members in electrical communication with the electrodes 122. In some embodiments, the electrical conductors may be disposed within a lumen of the elongate shaft 114 while in other embodiments, the electrical conductors may be embedded in a wall of the elongate shaft 114.

The ablation system 100 may further include a plurality of radially extending probes 130a, 130b (collectively 130). While FIG. 6 illustrates two radially extending probes 130, it is contemplated that the ablation system 100 may include any number of radially extending probes 130 desired, such as, but not limited to, one, two, three, four, or more. The probes 130 may extend proximally from a distal end region 136a, 136b (collectively 136) to a proximal end (not shown) configured to remain outside the body. The proximal ends may be individually manipulated to provide for independent longitudinal movement of the probes 130. In some embodiments, the distal end regions 136 of the probes 130 may be sharpened or pointed to facilitate the advancement of the probes 130 through tissue, although this is not required. In some embodiments, the distal end regions 136 may have a spear-like or arrow shape.

In some instances, the probes 130 may be formed from shape memory alloys, enabling the probes 130 to assume a curved profile when advanced distally from the delivery sheath 112, similar to probes 30 described above. For example, the probes 130 can be formed from alloys such as, but not limited to, nitinol or Elgiloy®. In some embodiments, the probes 130 may be formed from a conductive material covered with an insulating or semi-insulating coating 132a, 132b (collectively 132). The probes 130 may be coated with insulating material using any number of coating techniques, such as, but not limited to, dip coating, spray coating, etc. In some instances, the probes 130 may be coated with parylene or other insulating material. In some instances, the coating 132 may be formed of semi-insulating materials, such as but not limited to a porous polymer or a ceramic. It is further contemplated that the coating 132 may be a very thin polymer or coating.

It is contemplated that the coating 132 may be removed from or not applied to one or more locations on the probes 130 to form one or more electrode pads or electrically conductive regions 134a, 134b (collectively 134) configured to deliver RF energy to a target region. In some embodiments, the electrically conductive regions 134a, 134b may be formed at or adjacent to a distal end region 136a, 136b of the probes 130. While the probes 130 are illustrated as including a single electrically conductive region 134 on each probe 130, it is contemplated that more than one electrically conductive region 134 may be formed on each probe 130, as desired. It is further contemplated that the probes 130 need not include the same number of electrically conductive regions 134 on each probe.

The probes 130 may be slidably disposed within a lumen 141 of the delivery sheath 112 such that the probes 130a, 130b can be advanced distally and proximally retracted individually. In some embodiments, the delivery sheath 112 may include features to maintain a desired circumferential spacing of the probes 130. For example, the wall of the delivery sheath 112 may be formed with three separate lumens therein for advancing each of the probes 130a, 130b through. In other instances, an inner wall of the delivery sheath 112 may include protrusions or other aligning features to maintain a desired spacing of the probes 130.

The probes 130 may be formed from a shape memory material and having a curved distal portion 140a, 140b (collectively 140). In some embodiments, the probes 130 may be formed having a generally linear configuration. It is contemplated that the probes 130 may extend generally parallel to a longitudinal axis of the elongate shaft 114 or at an angle to the longitudinal axis of the elongate shaft 114. The probes 130 may be temporarily deformed to assume a generally straight configuration for advancement within the delivery sheath 112 to the desired treatment location. The delivery sheath 112 may be formed of a suitable material to maintain the probes 130 in a biased, or collapsed, configuration. As a probe 130 is advanced distally out of the delivery sheath 112 (or as the delivery sheath 112 is proximally retracted) the distal portion 140 may regain its curved configuration. The distal end region 136 may expand radially outward from the elongate shaft 114 as it is distally advanced out of the delivery sheath 112. It is contemplated that the radial distance between the distal end region and the elongate shaft 114 may be controlled in part by the length of the probe 130 extending from the delivery sheath 112 and the radius of curvature of the distal portion 140. It is contemplated that each of the probes 130a, 130b may have distal portions 140a, 140b with different degrees of curvatures such that each probe 130, when fully deployed, extends a different radial distance from the elongate shaft 114. As used herein, the term "fully deployed" indicates that the curved or shaped portion of the probe 130 is fully extended from the delivery sheath. This may allow a physician to customize the treatment region to more efficiently ablate non-spherical or non-uniform target regions. For example, when fully deployed, the first probe 130a may extend a first radial distance from the elongate shaft 114 and the second probe 130b may extend a second radial distance from the elongate shaft 114. In some embodiments, the first radial distance may be greater than the second radial distance. This is just an example. It is contemplated that the distal portions 140 of the probes 130 may be formed in any shape and having any radial distance in the fully deployed configuration desired. In some instances, the probes 130 may be formed with distal portions 140 having similar or the same degrees of curvature.

In some embodiments, the electrically conductive regions 134a, 134b may be electrically connected individually to a power and control element through separate electrical conductors. In some instances, the electrical conductors may be an extension of the probes 130. In other instances, the electrical conductors may be separate members in electrical communication with the probes 130 and the electrically conductive regions 134.

Each electrode 122a, 122b, 122c and each electrically conductive region 134a, 134b may be connected to individual channels of a control and power unit through separate electrical conductors. As each electrode 122a, 122b, 122c and each electrically conductive region 134a, 134b may be individually connected to a separate grounding in channels of the control and power unit; power may be individually supplied and adjusted. For example, it is contemplated that each channel may include a separate variable resistor for individually adjusting each individual circuit. It is contemplated that the control and power unit may include any number of channels desired such that the electrical connections between the control and power unit and the electrodes 122a, 122b, 122c and the electrically conductive regions 134a, 134b may be individually adjusted. It is further contemplated that a separate processor or processing unit may be supplied in addition to the control and power unit.

Figure 7:
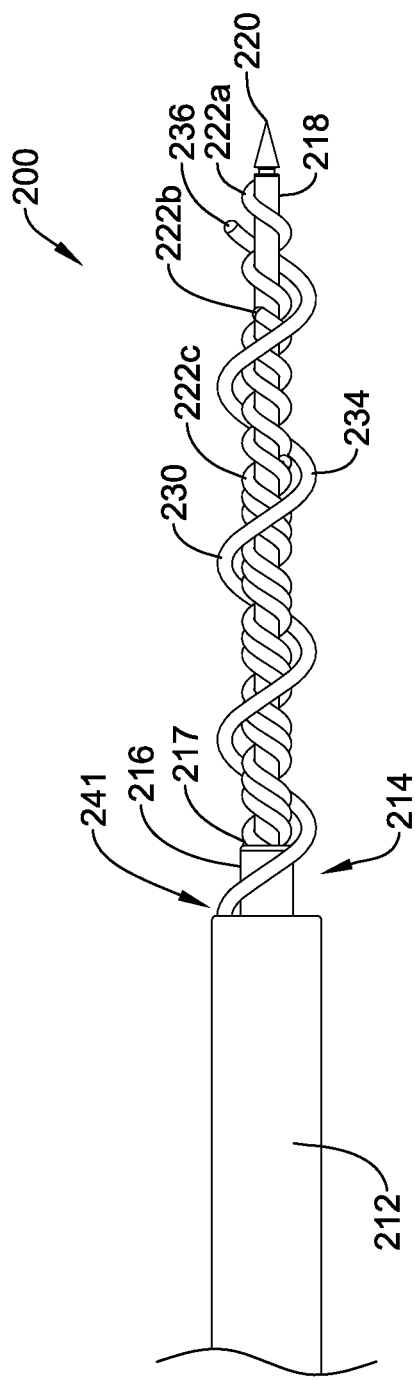
FIG. 7 is side view of a distal end of another illustrative multiple lead ablation system.

FIG. 7 is a side view of a distal end of another illustrative multiple lead ablation system 200 for use in ablating tissue. The system 200 may include an elongate shaft 214 slidably disposed within a lumen 241 of the delivery sheath or guide catheter 212. In some instances, the delivery sheath 212 may be advanced through a bronchoscope, endoscope, or gastroscope. In some instances, the elongate shaft 214 may have a proximal portion 216 and a distal portion 218. In some embodiments, the proximal portion 216 may have a larger cross-section than the distal portion 218, although this is not required. It is contemplated that in some embodiments, the elongate shaft 214 may have a uniform cross-section along the entire length thereof. The elongate shaft 214 may transition from a proximal portion 216 have a first cross-sectional area to a distal portion 218 have a second cross-sectional area in a step-wise manner or gradually transition. In some embodiments, the cross-sectional area for the proximal portion 216 may be larger than the cross-sectional area of the distal portion 218, although the reverse configuration is contemplated. The elongate shaft 214 may extend proximally from a distal end 220 to a proximal end (not shown) configured to remain outside the body. The proximal end may include a hub (not explicitly shown) attached thereto for connecting other treatment devices or providing a port for facilitating other treatments. It is contemplated that the stiffness of the elongate shaft 214 may be modified to form an ablation system 200 for use in various locations within the body. To this end, the material used for manufacturing the elongate shaft 214 may include any suitable biocompatible material such as, but are not limited to, polymers, metals, alloys, either in combination or alone. The distal end 220 of the elongate shaft 214 may be sharpened or pointed to facilitate the advancement of the elongate shaft 214 through tissue, although this is not required.

The ablation system 200 may further include a plurality of helically wound electrodes 222a, 222b, 222c (collectively 222) disposed about the distal portion 218 of the elongate shaft 214. The electrodes 222 may be similar in form and function to the electrodes 22 described above. While the system 200 is illustrated as including three helically wound electrodes 222, it is contemplated that the ablation system 200 may include any number of helically wound electrodes 222 desired, such as, but not limited to, one, two, three, or more. It is further completed that while the electrodes 222 are described as helically wound, other configurations are contemplated. For example, the electrodes 222 may extend generally parallel to a longitudinal axis of the elongate shaft 214. In other instances, the electrodes 222 may be discrete elements secured or otherwise formed on an outer surface of the elongate shaft 214. The electrodes 222 may be longitudinally and/or radially and/or circumferentially spaced as desired. The pitch (or distance between adjacent windings) of the electrodes 222 may be varied as desired.

It is contemplated that the electrodes 222 may extend over varying lengths of the distal portion 218 of the elongate shaft 214 to allow for customization of the treatment region. For example, the first helically wound electrode 222a may extend distally from a junction 117 between the proximal portion 216 and the distal portion 218 to a point proximal to the distal end 220 of the elongate shaft 214. The second helically wound electrode 222b may extend distally from the junction 117 between the proximal portion 216 and the distal portion 218 to a point proximal to a distal end of the first helically wound electrode 222a. The third helically wound electrode 222c may extend distally from the junction 117 between the proximal portion 216 and the distal portion 218 to a distal end proximal to a distal end of the second helically wound electrode 222b. In some instances, the electrodes 222 may extend proximally beyond the junction 117, although this is not required. The electrodes 222 may be formed from any suitable material such as, but not limited to, platinum, gold, stainless steel, cobalt alloys, or other non-oxidizing materials. In some instances, titanium, tantalum, or tungsten may be used. Portions of the electrodes 222 may be coated with an insulating or semi-insulating coating with regions of the coating removed to create conductive regions. In some instances, the electrodes 222 may be coated with parylene or other insulating material. In other instances, the coating may be formed of semi-insulating materials, such as but not limited to a porous polymer or a ceramic. It is further contemplated that the coating may be a very thin polymer or coating. The coating may electrically isolate the electrodes 222a, 222b, 222c from one another and allow for independent control of the each of the electrodes 222a, 222b, 222c.

In some embodiments, the electrodes 222a, 222b, 222c may be electrically connected individually to a power and control element through separate electrical conductors. In some instances, the electrical conductors may be an extension of the helically wound electrodes 222. In other instances, the electrical conductors may be separate members in electrical communication with the electrodes 222. In some embodiments, the electrical conductors may be disposed within a lumen of the elongate shaft 214 while in other embodiments, the electrical conductors may be embedded in a wall of the elongate shaft 214.

The ablation system 200 may further include a radially expanding probe 230. While the ablation system 200 is illustrated as including one radially expanding probe 230, it is contemplated that the ablation system 200 may include any number of radially expanding probes 230 desired, such as, but not limited to, one, two, three, four, or more. In some embodiments, the radially expanding probe 230 may include a helically wound filament. A proximal end of the probe 230 may be manipulated to provide for independent longitudinal movement of the probe 230. In some embodiments, the distal end region 236 of the probe 230 may be sharpened or pointed to facilitate the advancement of the probe 230 through tissue, although this is not required.

In some instances, the probe 230 may be formed from shape memory alloys, enabling the probe 230 to assume an expanded profile when advanced distally from the delivery sheath 212. The probe 230 may be slidably disposed within a lumen 241 of the delivery sheath 212 such that the probe 230 can be advanced distally and proximally retracted individually. For example, the probe 230 can be formed from alloys such as, but not limited to, nitinol or Elgiloy®. In some embodiments, the probe 230 may be formed from a conductive material covered with an insulating or semi-insulating coating (not explicitly shown). The probe 230 may be coated with insulating material using any number of coating techniques, such as, but not limited to, dip coating, spray coating, etc. In some instances, the probe 230 may be coated with parylene or other insulating material. In some instances, the coating may be formed of semi-insulating materials, such as but not limited to a porous polymer or a ceramic. It is further contemplated that the coating may be a very thin polymer or coating.

It is contemplated that the coating may be removed from or not applied to one or more locations on the probe 230 to form one or more electrode pads or electrically conductive regions 234 configured to deliver RF energy to a target region. In some embodiments, the electrically conductive region 234 may be formed at or adjacent to a distal end region 236 of the probe 230. In other embodiments, the conductive region 234 may extend along the entire length of the probe 230. While the probe 230 is illustrated as including a single electrically conductive region 234, it is contemplated that more than one electrically conductive region 234 may be formed on each probe 230, as desired.

The probe 230 may be formed from a shape memory material. In some instances, the probe 230 may be formed having a coiled or helical shape. The diameter of the probe 230 in an expanded configuration may be larger than a diameter of the delivery sheath 212, although this is not required. It is contemplated that the diameter of the probe 230 in the expanded configuration may be constant over the length of the probe 230 or may vary over the length of the probe 230. In some instances, the diameter of the probe 230 may increase from the proximal end to the distal end thereof or may decrease from the proximal end to the distal end thereof. It is contemplated that the diameter of the probe 230 may transition in gradual, sloping manner or in a step-wise manner. The probe 230 may be compressed into a collapsed configuration within the delivery sheath 212 for delivery to the treatment region. The delivery sheath 212 may be formed of a suitable material to maintain the probe 230 in a biased, or collapsed, configuration. As the probe 230 is advanced distally out of the delivery sheath 212 (or as the delivery sheath 212 is proximally retracted) the probe 230 may regain its expanded configuration. The probe 230 may expand radially outward from the elongate shaft 214 as it is distally advanced out of the delivery sheath 212.

In some embodiments, the electrically conductive regions 234 may be electrically connected to a power and control element through an electrical conductor. In some instances, the electrical conductor may be an extension of the probe 230. In other instances, the electrical conductors may be a separate member in electrical communication with the probe 230 and the electrically conductive region 234.

Each electrode 222a, 222b, 222c and each electrically conductive region 234 may be connected to individual channels of a control and power unit through separate electrical conductors. As each electrode 222a, 222b, 222c and each electrically conductive region 234 may be individually connected to a separate grounding in channels of the control and power unit; power may be individually supplied and adjusted. For example, it is contemplated that each channel may include a separate variable resistor for individually adjusting each individual circuit. It is contemplated that the control and power unit may include any number of channels desired such that the electrical connections between the control and power unit and the electrodes 222a, 222b, 222c and the electrically conductive regions 234 may be individually adjusted. It is further contemplated that a separate processor or processing unit may be supplied in addition to the control and power unit.

Systems 10, 100, 200 may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B 2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. In some other embodiments, a superelastic alloy, for example a superelastic nitinol can be used to achieve desired properties.

In at least some embodiments, portions or all of systems 10, 100, 200 may also be doped with, made of, or otherwise include a radiopaque material. Radiopaque materials are generally understood to be materials which are opaque to RF energy in the wavelength range spanning x-ray to gamma-ray (at thicknesses of <0.005"). These materials are capable of producing a relatively dark image on a fluoroscopy screen relative to the light image that non-radiopaque materials such as tissue produce. This relatively bright image aids the user of systems 10, 100, 200 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of systems 10, 100, 200 to achieve the same result.

In some embodiments, a degree of Magnetic Resonance Imaging (MRI) compatibility is imparted into systems 10, 100, 200. For example, systems 10, 100, 200 or portions thereof, may be made of a material that does not substantially distort the image and create substantial artifacts (i.e., gaps in the image). Certain ferromagnetic materials, for example, may not be suitable because they may create artifacts in an MRI image. Systems 10, 100, 200 or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Some examples of suitable polymers for systems 10, 100, 200 may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A tissue ablation system, comprising:
    a delivery sheath having a proximal end, a distal end, and a lumen extending therebetween;
    an elongate shaft having a proximal end and a distal end slidably disposed within the lumen of the delivery sheath;
    a plurality of helical members disposed about the elongate shaft, the plurality of helical members including a first helical member and a second helical member distinct from the first helical member, the plurality of helical members defining at least one helically wound electrode;
    wherein the first helical member and the second helical member axially overlap;
    one or more probes slidably disposed within the delivery sheath; and
    at least one electrically conductive region on the one or more probes.

2. The tissue ablation system of claim 1, wherein the one or more probes are configured to transform from a collapsed configuration to a radially expanded configuration when the one or more probes are distally advanced beyond the distal end of the delivery sheath.

3. The tissue ablation system of claim 2, wherein the one or more probes comprises a shape memory alloy.

4. The tissue ablation system of claim 3, wherein the one or more probes comprise an insulating coating disposed over the shape memory alloy.

5. The tissue ablation system of claim 4, wherein the at least one electrically conductive region on the one or more probes are regions of the probe free of the insulating coating.

6. The tissue ablation system of claim 1, wherein the one or more probes are individually actuatable.

7. The tissue ablation system of claim 1, wherein the at least one helically wound electrode and the at least one electrically conductive region on the one or more probes are electrically connected to a power and control unit through individual channels.

8. The tissue ablation system of claim 1, wherein a distal end region of the one or more probes comprises a spear-like shape.

9. The tissue ablation system of claim 1, wherein the one or more probes comprises a helically wound filament.

10. A tissue ablation system, comprising:
    a delivery sheath having a proximal end, a distal end, and a lumen extending therebetween;
    an elongate shaft having a proximal portion and a distal portion, the elongate shaft slidably disposed within the lumen of the delivery sheath;
    a first helical member defining a first helically wound electrode disposed about the distal portion of the elongate shaft, the first helically wound electrode having a first length;
    a second helical member defining a second helically wound electrode disposed about the distal portion of the elongate shaft, the second helically wound electrode having a second length less than the first length;
    wherein the second helical member is structurally distinct from the first helical member;
    wherein the first helical member is at least partially nested with the second helical member;
    a third helical member defining a third helically wound electrode disposed about the distal portion of the elongate shaft, the third helically wound electrode having a third length less than the second length;
    a plurality probes slidably disposed within the delivery sheath, the plurality of probes configured to move between a compressed configuration and an expanded configuration;
    at least one electrically conductive region on each of the probes of the plurality of probes; and
    a power and control unit in electrically communication with the first helically wound electrode, the second helically wound electrode, the third helically wound electrode, and the at least one electrically conductive region on the each of the probes of the plurality of probes.

11. The tissue ablation system of claim 10, wherein the at least the first helically wound electrode, the second helically wound electrode, the third helically wound electrode, and the at least one electrically conductive region on the each of the probes of the plurality of probes are electrically connected to the power and control unit through individual channels.

12. The tissue ablation system of claim 10, wherein each of the probes of the plurality of probes is individually slidable within the delivery sheath.

13. The tissue ablation system of claim 10, wherein plurality of probes are configured to transform from a collapsed configuration to a radially expanded configuration when the one or more probes are distally advanced beyond the distal end of the delivery sheath.

14. The tissue ablation system of claim 13, wherein the plurality of probes comprise shape memory alloy and an insulating coating disposed over the shape memory alloy.

15. The tissue ablation system of claim 10, wherein the distal portion of the elongate shaft comprises a piercing element.

\* \* \* \* \*